United States Patent [19]

Van Ooyen et al.

[11] Patent Number: 5,705,375
[45] Date of Patent: Jan. 6, 1998

[54] TRANSGENIC PLANTS HAVING A MODIFIED CARBOHYDRATE CONTENT

[75] Inventors: Albert Johannes Joseph Van Ooyen, Voorburg; Krijn Rietveld, Vlaardingen; Wilhelmus Johannes Quax, Voorschoten; Petrus Josephus Maria Van Den Elzen, Voorhout; Jan Pen, Leiden; Andreas Hoekema, Oegstgeest; Peter Christiaan Sijmons, Amsterdam, all of Netherlands

[73] Assignee: MOGEN International, N.V., Netherlands

[21] Appl. No.: 253,575

[22] Filed: Jun. 3, 1994

Related U.S. Application Data

[63] Continuation of Ser. No. 849,422, Jun. 12, 1992, abandoned.

[30] Foreign Application Priority Data

Sep. 13, 1990 [EP] European Pat. Off. ............ 90202438

[51] Int. Cl.$^6$ .................... C12N 15/82; C12N 15/56; C12N 1/21; A01H 5/00
[52] U.S. Cl. .................. 435/172.3; 435/95; 435/96; 435/201; 435/202; 435/205; 435/252.3; 435/320.1; 435/375; 800/205; 536/23.7; 536/24.1; 536/24.5
[58] Field of Search ................. 800/205, DIG. 9, 800/13, 37, 42–44, 56; 435/172.3, 320.1, 95, 200, 202, 209, 205, 375, 96, 252.3; 536/23.7, 24.1, 24.5

[56] References Cited

FOREIGN PATENT DOCUMENTS

| | | |
|---|---|---|
| 0275704 | 1/1990 | Germany . |
| WO 89/89145 | 9/1989 | WIPO . |
| WO 90/01551 | 2/1990 | WIPO . |
| 9010076 | 9/1990 | WIPO .............. C12N 15/82 |
| WO 90/12876 | 11/1990 | WIPO . |
| WO 91/14772 | 10/1991 | WIPO . |

OTHER PUBLICATIONS

Teeri et al., "Gene fusion to lacZ reveal new expression patterns of chimeric genes in transgenic plants" *EMBO J.* (1989) 8(2):343–350.

Laliberte et al., "The Xylanase Introns from *Cryptococcus albidus* Are Accurately Spliced in Transgenic Tobacco Plants", *Plant Molec. Biol.*, 18:447–51 (1992).

H.Q. Li et al. Nature Biotech. (Jun. 14, 1996) 14:736–40.

C. Schopke et al. Nature Biotech (Jun. 14, 1996) 14:731–735.

L. Hoffman et al. Plant Mol. Biol. ('88) 11:717–29.

T. Ohzani et al. Plant Mol. Biol. ('91) 16:117–28.

B. Larkins et al J. Cell. Biochem. Suppl. O (9 Part C) :264 (1985).

K. Hubus et al. Bio/Technology, vol. 13 (Jan. 13, 1995) pp. 63–66.

Hippe, S. et al. European J. of Cell Biol., vol. 50 (1989) pp. 230–234.

Kay, R., et al. Science, vol. 236 (1987) pp. 1299–1302.

Chrispeels, M. Ann. Rev. Plant Physiol. Plant Molec. Biol., vol. 42 (1991) pp. 1–23 or numbered in proof provided.

J. Giovannoni et al. The Plant Cell, vol. 1, (Jan. '89) pp. 53–63.

S. Ortlepp et al. Gene, vol. 23 ('83) pp. 267–276.

E. Bud et al. EMBO J., vol. 3 #5 ('84) pp. 1097–1102.

T. Caspar et al. PNAS, vol. 86 (Aug. '89) pp. 5830–5833.

P. Schreier et al. EMBO J., vol. 4 #1 (85) pp. 25–32.

R. Kay et al. Science, vol. 236, ('87) pp. 1299–1302.

*Primary Examiner*—Charles C. P. Rories
*Attorney, Agent, or Firm*—Morrison & Foerster LLP

[57] ABSTRACT

The present invention provides plants with a modified taste, solids content and/or texture. The invention also provides methods of obtaining such plants via transformation with DNA constructs containing genes encoding enzymes capable of degrading plant polysaccharides and optionally additional genes encoding enzymes which are capable of further modifying the degradation products resulting from the first degradation step.

17 Claims, 7 Drawing Sheets

```
XbaI
    *
TCTAGAGTC ATGAAACAAC AAAAACGGCT TTACGCCCGA TTGCTGACGC TGTTATTTGC
                          PstI                    HgaI      HgaI
GCTCATCTTC TTGCTGCCTC ATTCTGCAGC AGCGGCGGCA AATCTTAATG GGACGCTGAT
GCAGTATTTT GAATGGTACA TGCCCAATGA CGGCCAACAT TGGAAGCGTT TGCAAAACGA
CTCGGCATAT TTGGCTGAAC ACGGTATTAC TGCCGTCTGG ATTCCCCCGG CATATAAGGG
AACGAGCCAA GCGGATGTGG GCTACGGTGC TTACGACCTT TATGATTTAG GGAGTTTCA
TCAAAAAGGG ACGGTTCGGA CAAAGTACGG CACAAAAGGA GAGCTGCAAT CTGCGATCAA
AAGTCTTCAT TCCCGCGACA TTAACGTTTA CGGGGATGTG GTCATCAACC ACAAAGGCGG
CGCTGATGCG ACCGAAGATG TAACCGCGGT TGAAGTCGAT CCCGCTGACC GCAACCGCGT
AATTTCAGGA GAACACCTAA TTAAAGCCTG GACACATTTT CATTTTCCGG GGCGGGCAG
CACATACAGC GATTTTAAAT GGCATTGGTA CCATTTTGAC GGAACCGATT GGGACGAGTC
CCGAAAGCTG AACCGCATCT ATAAGTTTCA AGGAAAGGCT TGGGATTGGG AAGTTCCAA
TGAAAACGGC AACTATGATT ATTTGATGTA TGCCGACATC GATTATGACC ATCCTGATGT
CGCAGCAGAA ATTAAGAGAT GGGCACTTG GTATGCCAAT GAACTGCAAT TGGACGGTTT
CCGTCTTGAT GCTGTCAAAC ACATTAAATT TCTTTTTTG CGGGATTGGG TTAATCATGT
CAGGGAAAAA ACGGGGAAGG AAATGTTTAC GTAGCTGAA TATTGGCAGA ATGACTTGGG
```

FIG. 2A

```
CGGGCTGGAA AACTATTTGA ACAAAACAAA TTTTAATCAT TCAGTGTTTG ACGTGCCGCT
TCATTATCAG TTCCATGCTG CATCGACACA GGGAGGCGGC TATGATATGA GGAAATTGCT
GAACGGTACG GTCGTTTCCA AGCATCCGTT GAAATCGGTT ACATTGTCG  ATAACCATGA
                               SalI
TACACAGCCG GGGCAATCGC TTGAGTCGAC TGTCCAAACA TGGTTTAAGC CGCTTGCTTA
CGCTTTTATT CTCACAAGGG AATCTGATA  CCCTCAGGTT TTCTACGGGG ATATGTACGG
GACGAAAGGA GACTCCCAGC GCGAAATTCC TGCCTTGAAA CACAAAATTG AACCGATCTT
AAAAGCGAGA AAACAGTATG CGTACGGAGC ACAGCATGAT TATTTCGACC ACCATGACAT
TGTCGGCTGG ACAAGGGAAG GCGACAGCTC GGTTGCAAAT TCAGGTTTGG CGGCATTAAT
AACAGACGGA CCCGGTGGGG CAAAGCGAAT GTATGTCGGC GCCGGTGTC  CCGGTGAGAC
ATGGCATGAC ATTACCGGAA ACCGTTCGGA ACCGTTCGGA ATCAATTCGG AAGGCTGGGG
AGAGTTTCAC GTAAACGGCG GGTCGGTTTC AATTTATGTT CAAAGATAGA AGAGCAGAGA
      BamHI
GGACGGATTT CCTGAAGGAA ATCCGTTTTT TTATTTTGCC CGTCTTATAA ATTTCTTTGA
TTACATTTTA TAATTAATTT TAACAAAGTG TCATCAGCCC TCAGGAAGGA CTTGCTGACA
GTTGAATCG  CATAGGTAAG GCGGGGATGA AATGGCAACG TTATCTGATG TAGCAAAGAA
                                      BclI
AGCAAATGTG TCGAAAATGA CGGTATCGCG GGTGATCA
```

FIG. 2B

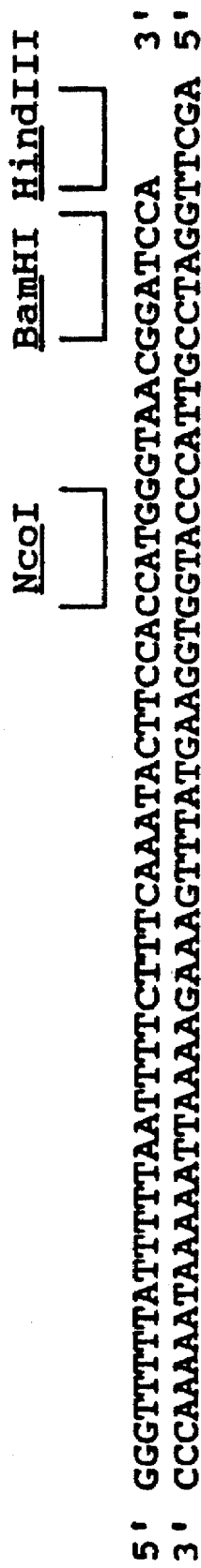
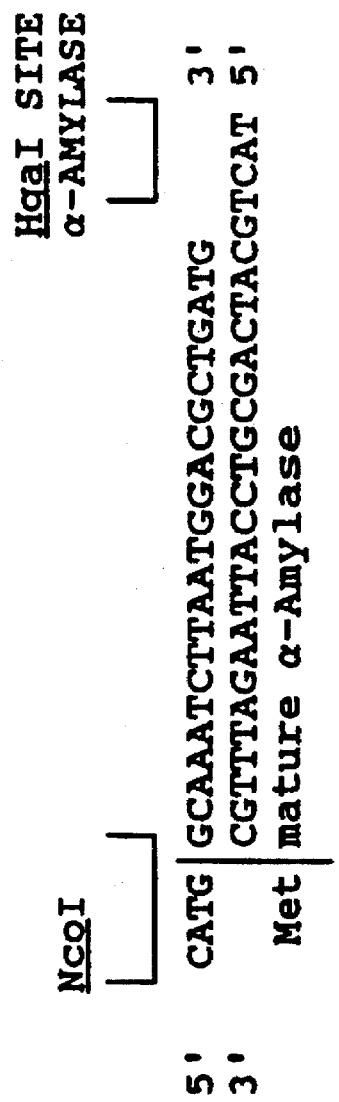
FIG. 3

5,705,375

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 1777 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
TCTAGAGTCA TGAAACAACA AAAACGGCTT TACGCCCGAT TGCTGACGCT GTTATTTGCG        60
CTCATCTTCT TGCTGCCTCA TTCTGCAGCA GCGGCGGCAA ATCTTAATGG GACGCTGATG       120
CAGTATTTTG AATGGTACAT GCCCAATGAC GGCCAACATT GGAAGCGTTT GCAAAACGAC       180
TCGGCATATT TGGCTGAACA CGGTATTACT GCCGTCTGGA TTCCCCGGC  ATATAAGGGA       240
ACGAGCCAAG CGGATGTGGG CTACGGTGCT TACGACCTTT ATGATTAGG  GGAGTTTCAT       300
CAAAAAGGGA CGGTTCGGAC AAAGTACGGC ACAAAAGGAG AGCTGCAATC TGCGATCAAA       360
AGTCTTCATT CCCGCGACAT TAACGTTTAC GGGGATGTGG TCATCAACCA CAAGGCGGC       420
GCTGATGCGA CCGAAGATGT AACCGCGGTT GAAGTCGATC CCGCTGACCG CAACCGCGTA       480
ATTTCAGGAG AACACCTAAT TAAAGCCTGG ACACATTTTC ATTTCCGGG  GCGCGGCAGC       540
ACATACAGCG ATTTTAAATG GCATTGGTAC CATTTTGACG GAACCGATTG GGACGAGTCC       600
CGAAAGCTGA ACCGCATCTA TAAGTTTCAA GGAAAGGCTT GGGATTGGGA AGTTTCCAAT       660
GAAAACGGCA ACTATGATTA TTTGATGTAT GCCGACATCG ATTATGACCA TCCTGATGTC       720
GCAGCAGAAA TTAAGAGATG GGGCACTTGG TATGCCAATG AACTGCAATT GGACGGTTTC       780
CGTCTTGATG CTGTCAAACA CATTAAATTT TCTTTTTTGC GGGATTGGGT TAATCATGTC       840
AGGGAAAAAA CGGGGAAGGA AATGTTTACG GTAGCTGAAT ATTGGCAGAA TGACTTGGGC       900
GCGCTGGAAA ACTATTTGAA CAAAACAAAT TTTAATCATT CAGTGTTTGA CGTGCCGCTT       960
CATTATCAGT TCCATGCTGC ATCGACACAG GGAGGCGGCT ATGATATGAG GAAATTGCTG      1020
AACGGTACGG TCGTTTCCAA GCATCCGTTG AAATCGGTTA CATTTGTCGA TAACCATGAT      1080
ACACAGCCGG GGCAATCGCT TGAGTCGACT GTCCAAACAT GGTTAAGCC  GCTTGCTTAC      1140
```

```
GCTTTTATTC  TCACAAGGGA  ATCTGGATAC  CCTCAGGTTT  TCTACGGGGA  TATGTACGGG   1200

ACGAAAGGAG  ACTCCCAGCG  CGAAATTCCT  GCCTTGAAAC  ACAAAATTGA  ACCGATCTTA   1260

AAAGCGAGAA  AACAGTATGC  GTACGGAGCA  CAGCATGATT  ATTTCGACCA  CCATGACATT   1320

GTCGGCTGGA  CAAGGGAAGG  CGACAGCTCG  GTTGCAAATT  CAGGTTTGGC  GGCATTAATA   1380

ACAGACGGAC  CCGGTGGGGC  AAAGCGAATG  TATGTCGGCC  GGCAAACGC   CGGTGAGACA   1440

TGGCATGACA  TTACCGGAAA  CCGTTCGGAG  CCGGTTGTCA  TCAATTCGGA  AGGCTGGGGA   1500

GAGTTTCACG  TAAACGGCGG  GTCGGTTTCA  ATTTATGTTC  AAAGATAGAA  GAGCAGAGAG   1560

GACGGATTTC  CTGAAGGAAA  TCCGTTTTTT  TATTTGCCC   GTCTTATAAA  TTTCTTTGAT   1620

TACATTTTAT  AATTAATTTT  AACAAAGTGT  CATCAGCCCT  CAGGAAGGAC  TTGCTGACAG   1680

TTTGAATCGC  ATAGGTAAGG  CGGGGATGAA  ATGGAACGT   TATCTGATGT  AGCAAAGAAA   1740

GCAAATGTGT  CGAAAATGAC  GGTATCGCGG  GTGATCA                              1777
```

( 2 ) INFORMATION FOR SEQ ID NO:2:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
GGGTTTTTAT  TTTTAATTTT  CTTTCAAATA  CTTCCACCAT  GGGTAACGGA  TCCA          54
```

( 2 ) INFORMATION FOR SEQ ID NO:3:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
AGCTTGGATC  CGTTACCCAT  GGTGGAAGTA  TTTGAAAGAA  AATTAAAAAT  AAAAACCC      58
```

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
CATGGCAAAT  CTTAATGGAC  GCTGATG                                           27
```

( 2 ) INFORMATION FOR SEQ ID NO:5:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
TACTGCATCA  GCGTCCATTA  AGATTTGC                                          28
```

( 2 ) INFORMATION FOR SEQ ID NO:6:

( i ) SEQUENCE CHARACTERISTICS:
        ( A ) LENGTH: 30 base pairs

```
          ( B ) TYPE: nucleic acid
          ( C ) STRANDEDNESS: single
          ( D ) TOPOLOGY: linear ( x i ) SEQUENCE DESCRIPTION: SEQ ID NO:6:

ATTAAGCTT ATGTTGCCAT ATAGAGTAGT                                              30

( 2 ) INFORMATION FOR SEQ ID NO:7:

( i ) SEQUENCE CHARACTERISTICS:
          ( A ) LENGTH: 31 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:7:

GTAGGATCCA TGGTGCAAAT GTTCAAAGTG T                                           31

( 2 ) INFORMATION FOR SEQ ID NO:8:

( i ) SEQUENCE CHARACTERISTICS:
          ( A ) LENGTH: 25 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:8:

CTTCCACCAT GGCGACCTTG GATTC                                                  25

( 2 ) INFORMATION FOR SEQ ID NO:9:

( i ) SEQUENCE CHARACTERISTICS:
          ( A ) LENGTH: 24 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:9:

AGCTCGAGCT CACCGCCAGG TGTC                                                   24

( 2 ) INFORMATION FOR SEQ ID NO:10:

( i ) SEQUENCE CHARACTERISTICS:
          ( A ) LENGTH: 9 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:10:

CATGGCGAC                                                                     9

( 2 ) INFORMATION FOR SEQ ID NO:11:

( i ) SEQUENCE CHARACTERISTICS:
          ( A ) LENGTH: 9 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:11:

CAAGGTCGC                                                                     9
```

TRANSGENIC PLANTS HAVING A MODIFIED CARBOHYDRATE CONTENT

This application is a file wrapper continuation of application Ser. No. 07/849,422, filed 12 Jun. 1992, now abandoned.

FIELD OF THE INVENTION

The present invention relates to the development of transgenic plants having a modified carbohydrate composition.

BACKGROUND OF THE INVENTION

It has long been an objective of the agriculture industry to develop crops having a modified carbohydrate composition, thus providing plants or plant organs more suitable for certain applications. Such modified crops provide plant products having a modified flavor, a higher content of desired saccharides and/or a more desirable texture. These crops may be either consumed directly or used in further processing.

In several plant species such as corn (Shannon & Garwood, 1984), pea (Bhattacharyya et al., 1990), potato (Hovenkamp-Hermelink et al., 1987), Arabidopsis (Caspar et al., 1985; Lin et al., 1988a; Lin et al., 1988b) and tobacco (Hanson et al., 1988), mutants with an altered carbohydrate composition have been found. This phenomenon may be attributable to mutations found mainly in enzymes involved in the regulation of the synthesis of starch. Some of these mutants are already used in the food industry, such as sweet corn (Shannon & Garwood, supra), which may be directly consumed.

Mutants altered in starch metabolism may be obtained via classical techniques such as random screening procedures and breeding. However, these methods are laborious and time consuming processes. Moreover, breeding may give rise to the phenotype that is screened for, but may lead to the loss of other desired characteristics, or the introduction of highly undesired characteristics (such as potatoes having a high alkaloid content). Changing plant characteristics through genetic engineering is a precise and predictable method, the nature of the gene which is spliced into the genome is known and no undesired genes are integrated simultaneously. Finally, modification of a specific characteristic, for instance, the alteration of the level or nature of certain products in the mutant is often difficult or even impossible using classical techniques. As such, genetic modification techniques have opened up new strategies and lead to new products that cannot be obtained by classical techniques.

It would be clearly advantageous to develop sophisticated and predictable methods for obtaining plants having a modified carbohydrate composition, based on genetical engineering techniques.

In U.S. Pat. No. 4,801,540, DNA fragments are disclosed encoding an enzyme capable of hydrolyzing poly (1,4-α-D galacturonide) glycan into galacturonic acid. Expression constructs are provided in which the structural gene encoding this enzyme is linked to modified regulatory regions in order to modulate the expression of the enzyme. The purpose of the invention as disclosed in the publication is to decrease expression levels of the polygalacturonase enzyme in order to inhibit the degradation of polygalacturonic acid and thus control fruit ripening.

In PCT application WO 89/12386, plants and methods are disclosed in which the carbohydrate content is modified through the expression, in planta, of enzymes such as sucrase and levan sucrase. The object of the invention is to increase the concentration of high molecular weight carbohydrate polymers in fruit in order to alter soluble solids and viscosity.

European Patent Application 438,904 describes the modification of plant metabolism (especially in tubers) whereby the level of phosphofructokinase activity is increased, resulting in significantly reduced levels of sucrose and reducing sugars accumulating in the tubers.

PCT application WO 90/12876 describes the regulation of endogenous α-amylase activity in genetically modified potato plants. The disclosure states that a reduction of potato α-amylase activity, and thus a reduction of the degradation of starch to reducing sugars is desirable for the production of potato chips as reducing sugars may be subjected to Maillard reactions during the frying of the potatoes which leads to a detrimental effect on the flavor and of the product. On the other hand, the disclosure states that a higher potato α-amylase activity, and thus a higher reducing sugar content is desired if the modified potato tubers are to be used for fermentation for the production of spirits.

SUMMARY OF THE INVENTION

The present invention provides transgenic plants or plant organs which have a modified polysaccharide composition, as well as methods for the production of such plants. This is achieved via the introduction into the plant of a DNA sequence encoding an enzyme which is capable of degrading plant polysaccharides.

The present invention also provides DNA expression constructs and vectors for the transformation of plants. The expression contructs are under the control of regulatory sequences which are capable of directing the expression of the selected polysaccharide modification enzymes. These regulatory sequences may also include sequences capable of directing the expression of the chosen enzymes at a desired developmental stage of the plant or plant organ and/or tissue specifically.

Furthermore, depending on the products desired in planta, one or more additional expression constructs may be introduced into the plant. These additional expression constructs contain DNA sequences encoding secondary enzymes which convert the degradation products resulting from the first enzymatic reaction to the desired oligo- or monosaccharides.

The transgenic plants provided by the present invention find applications as new products with a modified taste, solids content and/or more desirable texture.

BRIEF DESCRIPTION OF THE FIGURES

FIG. 2. Genomic, sequence (SEQ ID NO:1) of the α-amylase gene of *Bacillus licheniformis* as present in the vector pPROM54.

FIG. 3. Synthetic oligonucleotide duplexes (SEQ ID NO:4, SEQ ID NO:5) used for the various constructions.

DETAILED DESCRIPTION OF THE PREFERRED EMBODIMENTS

Figure 1:
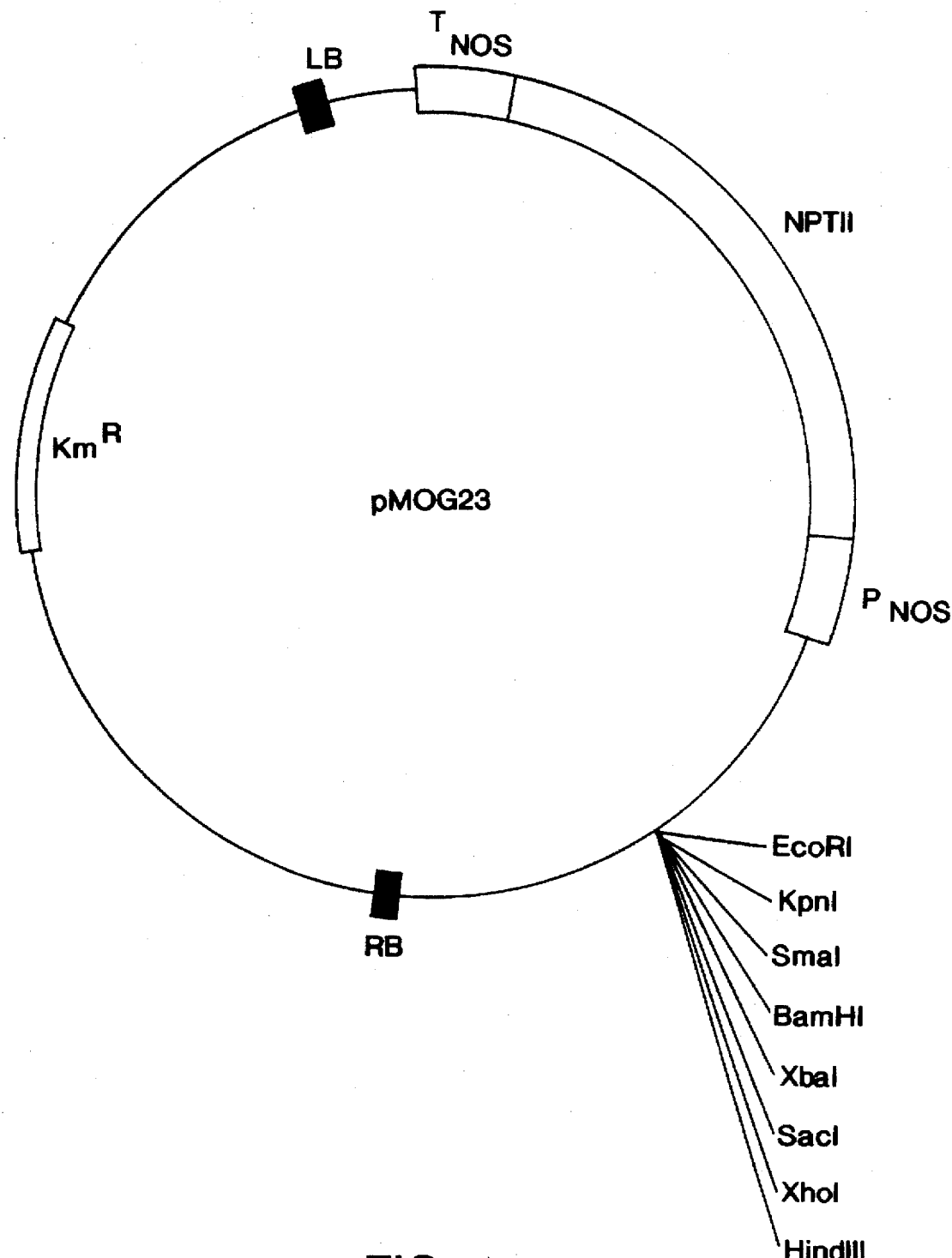
FIG. 1. Binary vector pMOG23.

The present invention provides transgenic plants or plant organs which have a modified polysaccharide composition and overcomes the disadvantages encountered in classical plant breeding techniques by the stable introduction into the plants of DNA sequences encoding certain enzymes which are capable of polysaccharide degradation.

It was found unexpectedly that the transformation of tobacco with a bacterial α-amylase gene (lacking a secretory signal sequence) resulted in the accumulation of maltodextrins such as maltose and maltotriose, which is indicative of α-amylase activity. This finding demonstrates that it is possible to modify polysaccharide composition in planta by the introduction and translation of a gene encoding a polysaccharide degrading enzyme.

The observed degradation of starch by the introduction of the α-amylase enzyme is very surprising since in plant cells, the entire process of starch synthesis occurs in the specific organelles chloroplasts, amyloplasts (or the like) where starch is stored, whereas the expressed α-amylase is expected to be present in the cytoplasm since no sequences were present to direct the α-amylase to these organelles. Certain starch degrading enzymes are endogenous to the cytoplasm of plant leaf cells. However, their function in the cytoplasm has never been conclusively explained and has never been correlated with the degradation of starch, in planta, because of the compartmental division of the two entities (Caspar et al., 1989; Lin et al., 1988 a,b and c; Okita et al., 1979).

According to the present invention, the extent to which the taste and/or texture of the plants is modified may be regulated using a variety of means including the choice of the saccharide modifying enzyme or enzymes, the choice of the regulatory regions of the DNA construct designed for the expression of the enzyme of interest and the targeting of the expressed enzyme to a pre-determined intracellular locus.

The choice of the enzyme or enzymes of interest is clearly of paramount importance in obtaining the desired final product. Should more than one enzyme of interest be expressed in a plant, the ratios of the respective enzymes may be chosen in order to obtain the optimal effect (e.g. the desired sweetness).

The regulation of the expression of the enzyme(s) of interest with respect to expression level and spatial (tissue/ organ specific) and/or developmental regulation of expression is also a means of obtaining an optimal product. For example, the type and strength of the promoter with respect to the timing and/or location of the expression of the enzyme(s) of interest will provide optimal levels of the enzyme(s) of interest in the desired locus of the transformed plant.

Finally, the locus (e.g. cellular compartment or organelle) to which the expressed enzyme may be targeted can be chosen so that an optimal effect, such as better access to the substrate, is obtained.

Variations in expression levels are sometimes observed as a result of varying copy number and/or site of integration of the transforming DNA. This natural variation may be used to select those individual plants from the pool of transgenic plants which have the desired characteristics in terms of sweetness, texture and the like. These individual plants can be used for multiplication and/or breeding with other varieties.

Combinations of the above measures may also be used to obtain the desired effect. Methods of obtaining optimal products may be determined by the skilled artisan using the teaching found below.

According to the present invention, (primary) enzymes of interest to be expressed in plants include any enzymes or combination of enzymes which are capable of degrading plant polysaccharides. Especially preferred are enzymes encoded by DNA sequences which are of microbial origin. If necessary, the coding and/or regulatory sequences may be modified to achieve cytoplasmic or organellar expression, tissue specificity or expression at a desired maturity stage of the plant or plant organ. Furthermore, codons may be modified to improve expression of the gene in the selected plant host.

Enzymes of interest capable of use in conjunction with the present invention include:

a) starch degrading enzymes such as 1) α-amylases (EC 3.2.1.1); 2) exo-1,4-α-D glucanases such as amyloglucosidases (EC 3.2.1.3), β-amylases (EC 3.2.1.2), α-glucosidases (EC 3.2.1.20), and other exo-amylases; and 3) starch debranching enzymes, such as isoamylase (EC 3.2.1.68), pullulanase (EC 3.2.1.41), and the like;

b) cellulases such as exo-1,4-β-cellobiohydrolase (EC 3.2.1.91), exo-1,3-β-D-glucanase (EC 3.2.1.39), glucosidase (EC 3.2.1.21) and the like;

c) endoglucanases such as endo-1,3-β-glucanase (EC 3.2.1.6) and endo-1,4-β-glucanase (EC 3.2.1.4) and the like;

d) L-arabinases, such as endo-1,5-α-L-arabinase (EC 3.2.1.99), α-arabinosidases (EC 3.2.1.55) and the like;

e) galactanases such as endo-1,4-β-D-galactanase (EC 3.2.1.89), endo-1,3-β-D-galactanase (EC 3.2.1.90), galactosidase (EC 3.2.1.22), β-galactosidase (EC 3.2.1.23) and the like;

f) mannanases, such as endo-1,4-β-D-mannanase (EC 3.2.1.78), β-mannosidase (EC 3.2.1.25), α-mannosidase (EC 3.2.1.24) and the like;

g) xylanases, such as endo-1,4-β-xylanase (EC 3.2.1.8), β-D-xylosidase (EC 3.2.1.37), 1,3-β-D-xylanase, and the like;

h) other enzymes such as α-L-fucosidase (EC 3.2.1.51), α-L-rhamnosidase (EC 3.2.1.40), levanase (EC 3.2.1.65), inulanase (EC 3.2.1.7), and the like.

Optionally, in a further embodiment, the present invention also contemplates the introduction to the target (host) plant of one or more additional DNA constructs encoding secondary enzymes of interest which are capable of further modifying the polysaccharide degradation products (obtained from the action of the primary polysaccharide degrading enzyme(s)) to desired saccharide subunits. Especially preferred secondary enzymes are enzymes encoded by DNA sequences which are of microbial origin.

To illustrate, secondary enzymes of particular interest, which are capable of further degrading the maltose, maltotriose and α-dextrins obtained from the first degradation of starch, include inter alia, maltases, α-dextrinase, α-1,6-glucosidases, and the like. The action of these enzymes result in the formation of glucose.

In yet a further embodiment of the present invention, if desired, one or more further secondary enzymes, which are capable of modifying monosaccharides, may be expressed in the same plant. Such enzymes include but are not limited to glucose isomerase, invertase, and the like.

The source from which DNA sequences encoding these enzymes of interest may be obtained is not relevant, provided the enzyme is active in the environment in which the enzyme is expressed or in which the expressed enzyme is targeted. The choice of both the primary (plant polysaccharide degrading) and, if desired, secondary enzymes of interest may depend on the substrate specificity and/or the desired saccharide end-product.

The enzymes of interest may be expressed constitutively in the transgenic plants during all stages of development. Depending on the use of the plant or plant organs, the enzymes may be expressed in a stage-specific manner, for instance during tuber formation or fruit development. Furthermore, depending on the use, the enzymes may be expressed tissue-specifically, for instance in plant organs such as fruit, tubers, leaves or seeds.

Plant polysaccharides, as defined within the context of the present invention are intended to consist of polyhydroxy aldehydes or ketones, consisting of more than six covalently-linked monosaccharides, which are normally found in plants prior to the action of the enzyme or enzymes of interest according to the present invention. Such polysaccharides are typically polymers of D-arabinose, D-fructose, D- and L-galactose, D-glucose, and D-xylose and mannose.

Saccharide subunits, the desired end-products of the present invention, are defined as saccharides having a shorter chain length than the original polysaccharide, including monosaccharides, which are obtained via the action of one or more enzymes of interest on the plant polysaccharides.

Transgenic plants, as defined in the context of the present invention include plants (as well as parts and cells of said plants) and their progeny which have been genetically modified using recombinant DNA techniques to cause or enhance production of at least one enzyme of interest in the desired plant or plant organ.

Plants capable of being used in conjunction with the present invention include, but are not limited to crops producing edible flowers such as cauliflower (*Brassica oleracea*), artichoke (*Cynara scolymus*), fruits such as apple (Malus, e.g. *domesticus*), banana (Musa, e.g. *acuminata*), berries (such as the currant, Ribes, e.g. *rubrum*), cherries (such as the sweet cherry, Prunus, e.g. *avium*), cucumber (Cucumis, e.g. *sativus*), grape (Vitis, e.g. *vinifera*), lemon (*Citrus limon*), melon (*Cucumis melo*), nuts (such as the walnut, Juglans, e.g. *regia*; peanut, Arachis *hypogeae*), orange (Citrus, e.g. *maxima*), peach (Prunus, e.g. *persica*), pear (Pyra, e.g. *communis*), pepper (Solanum, e.g. *capsicum*), plum (Prunus, e.g. *domestica*), strawberry (Fragaria, e.g. *moschata*), tomato (Lycopersicon, e.g. *esculentum*), leafs, such as alfalfa (Medicago, e.g. *sativa*), cabbages (such as *Brassica oleracea*), endive (Cichoreum, e.g. *endivia*), leek (Allium, e.g. *porrum*), lettuce (Lactuca, e.g. *sativa*), spinach (Spinacia e.g. *oleraceae*), tobacco (Nicotiana, e.g. *tabacum*), roots, such as arrowroot (Maranta, e.g. *arundinacea*), beet (Beta, e.g. *vulgaris*), carrot (Daucus, e.g. *carota*), cassava (Manihot, e.g. *esculenta*), turnip (Brassica, e.g. *rapa*), radish (Raphanus, e.g. *sativus*), yam (Dioscorea, e.g. *esculenta*), sweet potato (*Ipomoea batatas*) and seeds, such as bean (Phaseolus, e.g. *vulgaris*), pea (Pisum, e.g. *sativum*), soybean (Glycin, e.g. *max*), wheat (Triticum, e.g. *aestivum*), barley (Hordeum, e.g. *vulgare*), corn (Zea, e.g. *mays*), rice (Oryza, e.g. *sativa*), tubers, such as kohlrabi (Brassica, e.g. *oleraceae*), potato (Solanum, e.g. *tuberosum*), and the like.

The choice of the plant species is determined by the intended use of the plant or parts thereof and the amenability of the plant species to transformation.

The expression of recombinant genes in plants involves such details as transcription of the gene by plant polymerases, translation of mRNA, etc., which are known to persons skilled in the art of recombinant DNA techniques. Only details relevant for the proper understanding of this invention are discussed below.

Regulatory sequences which are known or are found to cause expression of a gene encoding an enzyme of interest in planta may be used in the present invention. The choice of the regulatory sequences used depends on the target crop and/or target organ of interest. Such regulatory sequences may be obtained from plants or plant viruses, or may be chemically synthesized. Such regulatory sequences are promoters active in directing transcription in plants, either constitutively or developmental stage- and/or tissue-specifically, depending on the use of the plant or parts thereof. These promoters include, but ate not limited to promoters showing constitutive expression, such as the 35S promoter of Cauliflower Mosaic Virus (CaMV) (Guilley et al., 1982), those for leaf-specific expression, such as the promoter of the ribulose bisphosphate carboxylase small subunit gene (Coruzzi et al., 1984), those for root-specific expression, such as the promoter from the glutamine synthase gene (Tingey et al., 1987), those, for seed-specific expression, such as the cruciferin A promoter from *Brassica napus* (Ryan et al., 1989), those for tuber-specific expression, such as the class-I patatin promoter from potato (Rocha-Sosa et al., 1989; Wenzler et al., 1989) or those for fruit-specific expression, such as the polygalacturonase (PG) promoter from tomato (Bird et al., 1988).

Other regulatory sequences such as terminator sequences and polyadenylation signals include any such sequence functioning as such in plants, the choice of which is within the level of the skilled artisan. An example of such sequences is the 3' flanking region of the nopaline synthase (nos) gene of *Agrobacterium tumefaciens* (Bevan, 1984).

The regulatory sequences may also include enhancer sequences, such as found in the 35S promoter of CaMV, and mRNA stabilizing sequences such as the leader sequence of Alfalfa Mosaic Virus (AlMV) RNA4 (Brederode et al., 1980) or any other sequences functioning in a like manner.

In one embodiment of the present invention, if simple expression of an enzyme of interest into the cytoplasm of the plant cell should be desired, the expressed enzyme should not contain a secretory signal peptide or any other targeting sequence.

In another embodiment of the present invention, the DNA construct encoding a selected enzyme of interest according to the present invention may optionally be provided with leader sequences capable of targeting the expressed enzyme to a predetermined locus in order to have better access of the enzyme to its substrate. Targeting sequences which may be operably coupled to the enzyme of interest in order to achieve this function have been described in the literature (Smeekens et al., 1990; van den Broeck et al., 1985; Schreier et al., 1985). For example, to obtain expression in chloroplasts and mitochondria, the expressed enzyme should contain a specific so-called transit peptide for import into these organelles (Smeekens et al., 1990). If the activity of the enzyme is desired in the vacuoles, a secretory signal sequence must be present, as well as a specific targeting sequence that directs the enzyme to these vacuoles (Tague et al., 1988). This may also lead to the targeting of the enzyme to seeds.

All parts of the relevant DNA constructs (promoters, regulatory-, stabilizing-, targeting- or termination sequences) of the present invention may be modified, if desired, to affect their control characteristics using methods known to those skilled in the art.

Several techniques are available for the introduction of the expression construct containing a DNA sequence encoding an enzyme of interest into the target plants. Such techniques include but are not limited to transformation of protoplasts using the calcium/polyethylene glycol method, electroporation and microinjection or (coated) particle bombardment (Potrykus, 1990).

In addition to these so-called direct DNA transformation methods, transformation systems involving vectors are widely available, such as viral vectors (e.g. from the Cauliflower Mosaic Virus (CaMV), Fraley et al., 1986) and bacterial vectors (e.g. from the genus Agrobacterium) (Potrykus, 1990). After selection and/or screening, the protoplasts, cells or plant parts that have been transformed can be regenerated into whole plants, using methods known in the art (Horsch, et al., 1985). The choice of the transformation and/or regeneration techniques is not critical for this invention.

For dicots, an embodiment of the present invention employs the principle of the binary vector system (Hoekema et al., 1983; Schilperoort et al., 1984) in which Agrobacterium strains are used which contain a vir plasmid with the virulence genes and a compatible plasmid containing the gene construct to be transferred. This vector can replicate in both *E.coli* and in Agrobacterium, and is derived from the binary vector Bin19 (Bevan, 1984) which is altered in details that are not relevant for this invention. The binary vectors as used in this example contain between the left- and right-border sequences of the T-DNA, an identical NPTII-gene coding for kanamycin resistance (Bevan, 1984) and a multiple cloning site to clone in the required gene constructs.

The transformation and regeneration of monocotyledonous crops is not a standard procedure. However, recent scientific progress shows that in principle monocots are amenable to transformation and that fertile transgenic plants can be regenerated from transformed cells. The development of reproducible tissue culture systems for these crops, together with the powerful methods for introduction of genetic material into plant cells has facilitated transformation. Presently the methods of choice for transformation of monocots are microprojectile bombardment of explants or suspension cells, and direct DNA uptake or electroporation of protoplasts. For example, transgenic rice plants have been successfully obtained using the bacterial hph gene, encoding hygromycin resistance, as a selection marker. The gene was introduced by electroporation (Shimamoto et al., 1989). Transgenic maize plants have been obtained by introducing the bar gene from *Streptomyces hygroscopicus*, which encodes phosphinothricin acetyltransferase (an enzyme which inactivates the herbicide phosphinothricin), into embryogenic cells of a maize suspension culture by microparticle bombardment (Gordon-Kamm et al., 1990). The introduction of genetic material into aleurone protoplasts of other monocot 2 crops such as wheat and barley has been reported (Lee et al., 1989). The stable transformation of wheat cell suspension cultures via microprojectile bombardment has recently been described (Vasil et al., 1991). Wheat plants have been regenerated from embryogenic suspension culture by selecting only the aged compact and nodular embryogenic callus tissues for the establishment of the embryogenic suspension cultures (Vasil et al., 1990). The combination of regeneration techniques with transformation systems for these crops enables the application of the present invention to monocots. These methods may also be applied for the transformation and regeneration of dicots.

If desired, a number of methods may be used to obtain transgenic plants in which more than one enzyme of interest is expressed. These include but are not limited to:

a. Cross-fertilization of transgenic plants each expressing a different enzyme of interest.

b. Plant transformation with a DNA fragment or plasmid that contains multiple genes, each encoding an enzyme of interest, each containing its own necessary regulatory sequences.

c. Plant transformation with different DNA fragments or plasmids simultaneously, each containing a gene for an enzyme of interest, using the necessary regulatory sequences.

d. Successive transformations of plants, each time using a DNA fragment or plasmid encoding a different enzyme of interest under the control of the necessary regulatory sequences.

e. A combination of the methods mentioned above. The choice of the above methods is not critical with respect to the objective of this invention.

In one embodiment of the present invention, an α-amylase is consititutively expressed intracellularly in tobacco and tomato plants, resulting in the degradation of starch in these plants to lower molecular weight saccharides. A genomic DNA fragment encoding mature α-amylase from *Bacillus licheniformis*, i.e. encoding the α-amylase without the signal peptide sequence, is placed under the control of the CaMV 35S promoter and enhancer sequences. The mRNA stabilizing leader sequence of RNA4 from AlMV is included, as well as the terminator and polyadenylation signal sequences of the nopaline synthase (nos) gene of *Agrobacterium tumefaciens*. The construct is thereafter subcloned into a binary vector such as pMOG23 (deposited at the Centraal Bureau voor Schimmelcultures, Baarn, the Netherlands on Jan. 29, 1990 under accession number CBS 102.90). This vector is introduced into *Agrobacterium tumefaciens* which contains a disarmed Ti-plasmid. Bacterial cells containing this construct are co-cultivated with tissues from the target plants, and transformed plant cells are selected on nutrient media containing antibiotics and induced to regenerate into differentiated plants on such media. The resulting plants contain the stably integrated gene and express the α-amylase intracellularly.

The α-amylase enzyme activity of the transgenic plants may be tested with direct enzyme assays using colorimetric techniques or gel assays. The assay of choice is not critical to the present invention. The protein is detectable on Western blots with antibodies raised against α-amylase from *Bacillus licheniformis*.

The plants may be qualitatively assayed for starch content either by staining for starch with iodine. Plants may be quantitatively assayed for the presence of starch degradation products by using techniques as NMR and HPLC. Other methods may also be used. The choice of the method is not critical to the present invention.

In another preferred embodiment, both an α-amylase and a glucoamylase are expressed in potatoes. The enzymes are expressed only in the tubers of the plants. The result is the degradation of starch in tubers by both enzymes to lower molecular weight saccharides. A genomic DNA fragment encoding mature α-amylase from *Bacillus licheniformis* and a cDNA fragment encoding mature glucoamylase from *Aspergillus niger* are each placed under the control of the tuber-specific promoter from a class-I patatin gene from potato. Both constructs also include the terminator and polyadenylation signal sequences of the nopaline synthase (nos) gene of *Agrobacterium tumefaciens*. Both constructs are thereafter subcloned together into the binary vector pMOG23. This vector is introduced into *Agrobacterium tumefaciens*, which contains a disarmed Ti plasmid. Bacterial cells containing this construct are cocultivated with tissues from potato plants and transformed plant cells are selected on nutrient media containing antibiotics, and induced to regenerate into differentiated plants on such media. The resulting plants contain the stably integrated genes. Both α-amylase and glucoamylase are expressed only in the tubers of the transformed potatoes. Both enzymes are expressed intracellularly.

The α-amylase and glucoamylase enzyme activities in the transgenic tubers can be tested with various assays. For example, glucoamylase activity may be determined by an assay measuring p-nitrophenol released from p-nitrophenol-α-D-glucopyranoside by the glucoamylase. Alpha-amylase activity may be measured as described above and in the examples provided below. The presence of both enzymes may be demonstrated by immunoblotting, for example. The choice of assays is not relevant to the present invention.

The transgenic potato tubers may be assayed for their carbohydrate composition by using techniques for the detection of sugars such as HPLC and NMR. Other methods may also be used. The choice of the method is not critical to the present invention.

Transgenic plants or plant organs (such as flowers, fruits, leaves, roots, tubers) having a higher content of polysaccharide degradation products and consequently a modified flavor and/or a desired texture, may be used as a new product either as such or in a form obtained after non-fermentative processing which retains the distinctive qualities resulting from the modification of the plant saccharides. Examples of such uses are the production of baby foods, juices, sauces, pastes, concentrates, sweeteners, jams, jellies, syrups, and animal feeds. Grains having an altered carbohydrate composition may be used in the productions of baked products, for example, which have a modified taste. Tobaccos having an altered carbohydrate composition exhibit a modified taste and aroma.

Alternatively, the polysaccharide degradation products may be extracted from the plant or plant organs and used as such, for instance as a sweetener, or in various processes.

The following examples are provided so as to give those of ordinary skill in the art a complete disclosure and description of how to make and use the invention and are not intended to limit the scope of what the inventors regard as their invention. Efforts have been made to ensure accuracy with respect to numbers used (e.g., amounts, temperature, pH, etc.) but some experimental errors and deviation should be accounted for. Unless indicated otherwise, temperature is in degrees Centigrade and pressure is at or near atmospheric.

EXAMPLE 1

Construction of the Binary Vector pMOG23

The binary vector pMOG23 (deposited at the Centraal Bureau voor Schimmelcultures, Baarn, The Netherlands, on Jan. 29, 1990, under accession number CBS 102.90; shown in FIG. 1) is a derivative of vector Bin19 (Bevan, 1984). First, the positions of the left border (LB) and the right border (RB) were interchanged with reference to the neomycin phosphotransferase gene II (NPTII gene). Secondly, the orientation of the NPTII gene was reversed giving transcription in the direction of LB. Finally, the polylinker of Bin19 was replaced by a polylinker having the following restriction enzyme recognition sites: EcoRI, KpnI, SmaI, BamHI, XbaI, SacI, XhoI, and HindIII.

EXAMPLE 2

Cloning of the α-amylase Gene of *Bacillus licheniformis*

All transformations in this example were performed in *E. coli* strain DH5α.

a. Tailoring of the α-amylase gene of *Bacillus licheniformis*

The α-amylase gene (FIG. 2) from *Bacillus licheniformis* is present in the Bacillus vector pPROM54, which is described in European Patent Application 224,294, the disclosure of which is hereby incorporated by reference. The plasmid 2 pPROM54 has been deposited at the Centraal Bureau voor Schimmelcultures, Baarn, The Netherlands on Nov. 5, 1985, under accession number CBS 696.85.

The plasmid pPROM54 was digested with XbaI and BclI. The XbaI/BclI fragment was cloned in plasmid pUC18 digested with XbaI and BamHI, resulting in plasmid pMOG318. A SalI/BamHI fragment was synthesized with pMOG318 as a template with PCR technology, creating the BamHI site by use of a mismatch primer (the position of the created BamHI site is indicated in FIG. 2). The SalI/BamHI PCR fragment was cloned in plasmid pIC-19R (Marsh et al., 1984) digested with SalI and BamHI, resulting in plasmid pMOG319. The SalI fragment from pMOG318 (the second SalI site is present in pUC18), containing the 5' end of the α-amylase gene, was cloned in pMOG319 digested with SalI. This resulted in plasmid pMOG320 which contains the entire α-amylase gene.

Construction of vector pMOG18

The expression cassette of pROKI (Baulcombe et al., 1986) was cloned as an EcoRI/HINDIII fragment into pUC18. This cassette contains the 800 bp Cauliflower Mosaic Virus (CaMV) 35S promoter fragment on an EcoRI/BamHI fragment and the nopaline synthase (nos) transcription terminator of *Agrobacterium tumefaciens* on a BamHI/HindIII fragment. The promoter fragment consists of the sequence from −800 to +1 (both inclusive) of the CaMV promoter. Position +1 is the transcription initiation site (Guilley et al., 1982). The sequence upstream of the NcoI site at position −512 was deleted and this site was changed into an EcoRI Site. This was achieved by cutting the expression cassette present in pUC18 with NcoI, filling in the single-stranded ends with Klenow polymerase and ligation of an EcoRI linker.

The resulting plasmid was cut with EcoRI, resulting in the deletion of the EcoRI fragment carrying the sequences of the CaMV 35S promoter upstream of the original NcoI site. The BamHI/HindIII fragment, containing the nos terminator was replaced by a synthetic DNA fragment (Oligonucleotide duplex A, FIG. 3) containing the leader sequence of RNA4 of Alfalfa Mosaic Virus (AlMV) (Brederode et al., 1980). This was done by cleavage with BamHI, followed by cleavage with HindIII and ligation of the synthetic DNA fragment. The BamHI site and three upstream nucleotides were deleted by site-directed mutagenesis.

In the resulting plasmid, the BamHI/HindIII fragment containing the nos terminator was reintroduced. The gene encoding beta-glucuronidase (originating from plasmid pRAJ 275; Jefferson, 1987) was ligated in as an NcoI/BamHI fragment, resulting in plasmid pMOG14.

Figure 4:
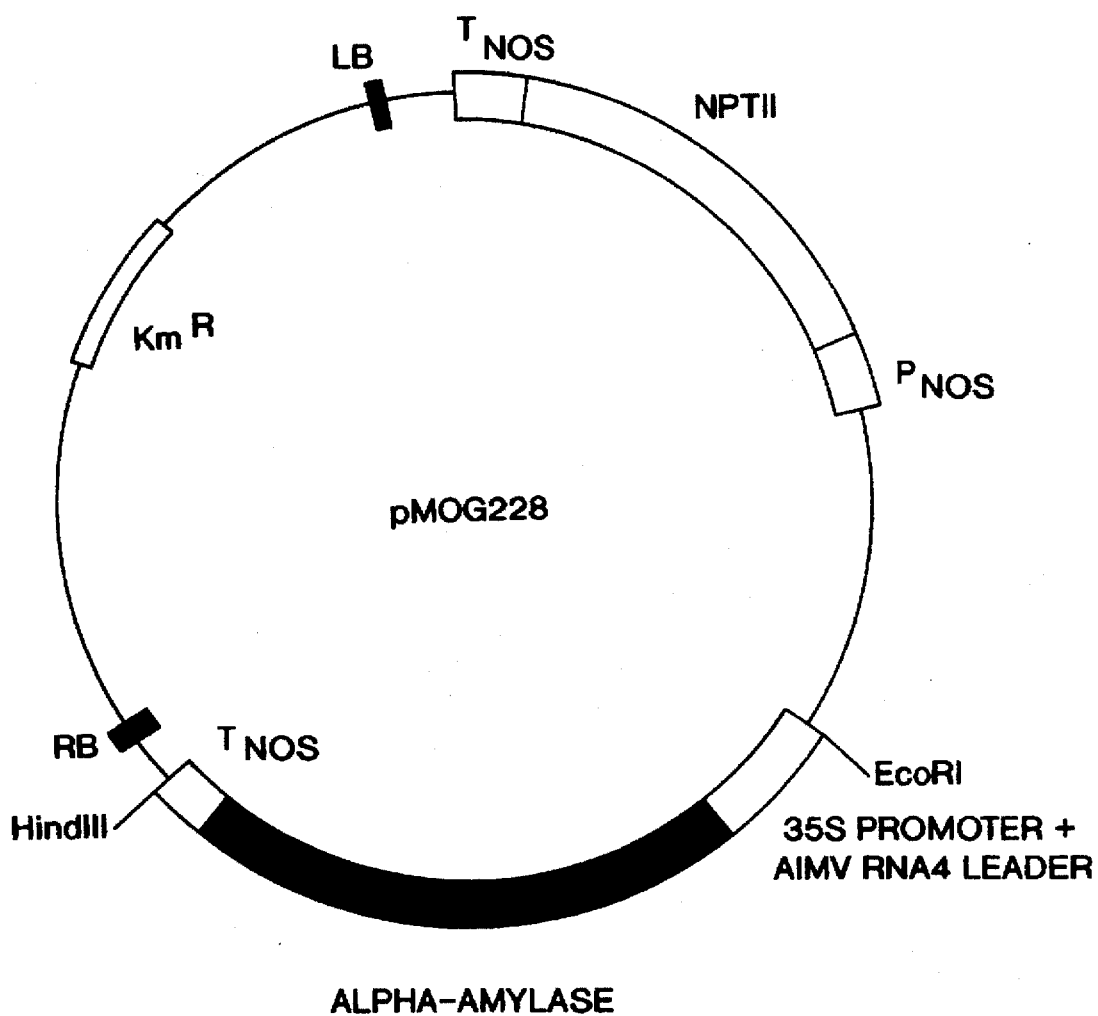
FIG. 4. Binary plasmid pMOG228, which comprises binary vector pMOG23 containing the genomic DNA sequence encoding mature α-amylase from *Bacillus licheniformis* preceded by a methionine translation initiation codon.

It is known that duplication of the sequence between −343 and −90 increases the activity of the CaMV 35S promoter (Kay et al., 1987). To obtain a promoter fragment with a double, so-called enhancer sequence, the enhancer fragment from plasmid pMOG14 was isolated as an AccI/EcoRI fragment and subsequently blunt-ended with Klenow polymerase. The thus-obtained fragment was introduced in pMOG14 cut with EcoRI and blunt-ended, such that the border between the blunt-ended EcoRI and AccI sites generated a new EcoRI site. The resulting plasmid pMOG18 contains the 35S CaMV promoter with a double enhancer sequence, the leader sequence of RNA4 from AlMV and the nos terminator in an expression cassette still present as an EcoRI/HindIII fragment.

c. Cloning of the α-amylase gene from *Bacillus licheniformis* in the binary vector Plasmid pMOG320 was digested with HgaI and BamHI. The HgaI/BamHI fragment was cloned together with the synthetic oligonucleotide duplex B (FIG. 3) into pMOG18 digested with NcoI and BamHI, resulting in plasmid pMOG322. The β-glucuronidase gene was thus replaced by the coding sequence for the mature α-amylase of *Bacillus licheniformis* preceded by the ATG triplet encoding the methionine translation initiation codon. Plasmid pMOG18 contains the 35S promoter and enhancer of Cauliflower mosaic virus (CaMV), the nopalin synthase (nos) terminator from *Agrobacterium tumefaciens* and the RNA4 leader sequence of Alfalfa mosaic virus (AlMV). The resulting construct does not contain coding information for a signal peptide. The entire construct was spliced out with EcoRI and HindIII and transferred into the binary vector pMOG23 digested with EcoRI and HindIII. The resulting plasmid has been designated pMOG228 (FIG. 4).

The chimeric α-amylase gene on the binary plasmid pMOG228 was mobilized, in a triparental mating with the *E.coli* strain HB101 containing plasmid pRK2013 (Ditta et al., 1980), into Agrobacterium strain LBA4404, which contains a plasmid having the virulence genes necessary for T-DNA transfer to the plant (Hoekema et al., 1983).

EXAMPLE 3

Transformation of Tobacco

Tobacco (*Nicotiana tabacum* cv. Petit Havanna SR 1) was transformed by co-cultivation of plant leaf disks (Horsch et al., 1985) with *Agrobacterium tumefaciens*, containing the binary vector pMOG228 with the α-amylase gene. Transgenic plants were selected on kanamycin resistance. The transgenic plants were assayed for activity of the enzyme of interest. Plants expressing the α-amylase gene were analyzed more thoroughly and used in further experiments.

Leaf discs of about 5×5 mm were cut from leaves of axenically grown plants of *Nicotiana tabacum* cv. Petit Havanna SR1. The discs were floated for 20 minutes in MS-medium (Murashige & Skoog, 1962) containing 30 g/L sucrose with 1% (v/v) of a culture of *Agrobacterium tumefaciens* LBA4404 (pMOG228) ($10^9$ cells/ml). Subsequently, the discs were briefly dried on filter paper and transferred to plates containing solid medium consisting of MS-medium, containing 30 g/L sucrose, 7 g/L agar, 1 mg/L kinetin and 0.03 mg/L naphthyl acetic acid (NAA). Two days later, the discs were transferred to plates containing the same medium plus 500 mg/L carbenicillin. After one week, the discs were again transferred to plates containing the same medium, this time with about 50 mg/L kanamycin to select for transgenic shoots. Discs were transferred to fresh plates with three week intervals. Developing shoots were excised and transferred to pots containing solid medium consisting of MS-medium, containing 30 g/L sucrose, 100 mg/L kanamycin and 100 mg/L cefotaxime for root development. After roots have developed, the plants were transferred to the soil. The plants were tested for expression of the gene of interest.

EXAMPLE 4

Alpha-amylase Expression in Transgenic Tobacco Plants

Alpha-amylase activity was determined by the method described by Saito (1973) at 56° C. Units are defined in this case as the amount of enzyme giving a reduction of the absorbance at 690 nm by 10% in 10 minutes. Specific activity for the *Bacillus licheniformis* α-amylase was 8.7× $10^5$ U/mg protein. The tip of one of the top leafs (about 100 mg) was cut off and homogenized in 100 µl α-amylase assay buffer (Saito, 1973). The homogenate was spun down for 10 minutes in an Eppendorf centrifuge. The supernatant was collected and assayed for protein and α-amylase content. Control plants had levels of activity at or below the detection limit.

In the 62 transgenic plants obtained, the measured expression levels, as determined by the method of Saito (1973) varied between 0 and 3.29 U/µg protein. Based on the specific activity of the enzyme, these levels corresponded to 0–0.38% of the total amount of soluble protein. The average was 0.11% of the total amount of soluble protein. The protein was clearly present intracellularly, since no significant amount of α-amylase activity was detected in the extracellular fluid that was isolated by vacuum filtration of the leaves with buffer, followed by collection of the fluid by centrifugation (Sijmons et al., 1990). These results were confirmed with immunological detection of the *Bacillus licheniformis* α-amylase on Western blots, which demonstrated that the protein is indeed the desired α-amylase. Further confirmation was obtained by running extracts and extracellular fluid on polyacrylamide-SDS gels. After electrophoresis, the gels were incubated in 0.04M Tris/HCl pH 7.4 for 3 hours with 6 changes of buffer to renature the enzymes. The gels were overlayered with 0.25% potato Lintner starch, 0.75% agar in 0.05M Tris/HCl pH 7.4 containing 1 mM $CaCl_2$, incubated overnight at 37° C. and subsequently stained with 1 mM $I_2$/0.5M KI in water. Alpha-amylase activity was detected as a clear zone in the overlay (Lacks & Springhorn, 1980). In the transgenic plants, an α-amylase was detected having an apparent molecular weight of about 55,000 kDa, the same as that of the *Bacillus licheniformis* α-amylase.

Tobacco plants expressing α-amylase were pale light green (chlorotic) and somewhat retarded in growth as compared to control plants.

EXAMPLE 5

Carbohydrate Analysis of Transgenic Tobacco Plants

Qualitatively the starch content in transgenic tobacco leaves, collected at roughly the half-way point of the photoperiod, was determined by destaining the leaves overnight by shaking in 96% ethanol, followed by staining for starch with 5.7 mM $I_2$ and 43.3 mM KI in 0.2N HCl. Leaves containing starch stained black-blue, while leaves lacking starch stained brownish-yellow (Caspar et al., 1985).

Approximately 2.5 g portions of leaf material (stored in deep-freeze) obtained from control and transformed (good α-amylase expressors) plants were homogenized in 10 ml water at 4° C. with an ultra-turrax. Microscopic inspection revealed that no intact cells remained. After removal of the cell fragments by centrifugation, the glucose oligomer content in the green-colored supernatent was determined. The filtered samples were analyzed via HPLC on an Aminex HPX-42A column (300 mm×7.8 mm, 85° C.) using water as the eluent. The presence of maltose and maltotriose were detected in the samples of the transformed plants and not in the control (untransformed) plants. The results are shown in Table 1, below.

TABLE 1

Saccharides extracted from tobacco leaves and analyzed on an Aminex HPX-42A-HPLC column

| Preparation | Saccharide | mg Saccharide/g wet material |
| --- | --- | --- |
| Control | Maltotriose | undetectable |
|  | Maltose | undetectable |
| Transgenic | Maltotriose | 0.34 |
|  | Maltose | 1.73 |

EXAMPLE 6

Cloning of the α-amylase Gene of *Bacillus licheniformis* in a Tuber-specific Expression Construct All transformations in *E. coli* in this example were performed in strain DH5α.

To construct an expression cassette for tuber-specific expression, the promoter from a class-I patatin gene of potato (*Solanum tuberosum* cv. Bintje) is synthesized using PCR technology with isolated genomic DNA (Mettler, 1987) as a template. Class-I patatin genes show tuber-specific expression in potato. Both the coding and flanking sequences of several members of the patatin multigene family have been determined (Rocha-Sosa et al., 1989; Bevan et al., 1986; Mignery et al., 1988). Chimeric genes have been reported containing 5' flanking regions of a class-I patatin gene fused to β-glucuronidase, giving rise to tuber-specific expression of β-glucuronidase (Wenzler et al., 1989).

Two oligonucleotides corresponding to the sequence of the pAT21 and B33 genes (Mignery et al., 1989; Bevan et al., 1986), are synthesized, allowing the amplification of the class-I patatin 5' flanking region as a HindIII/NcoI fragment:

5' ATTAAAGCTTATGTTGCCATATAGAGTAGT 3'

5' GTAGGATCCATGGTGCAAATGTTCAAAGTGT 3'

Figure 5:
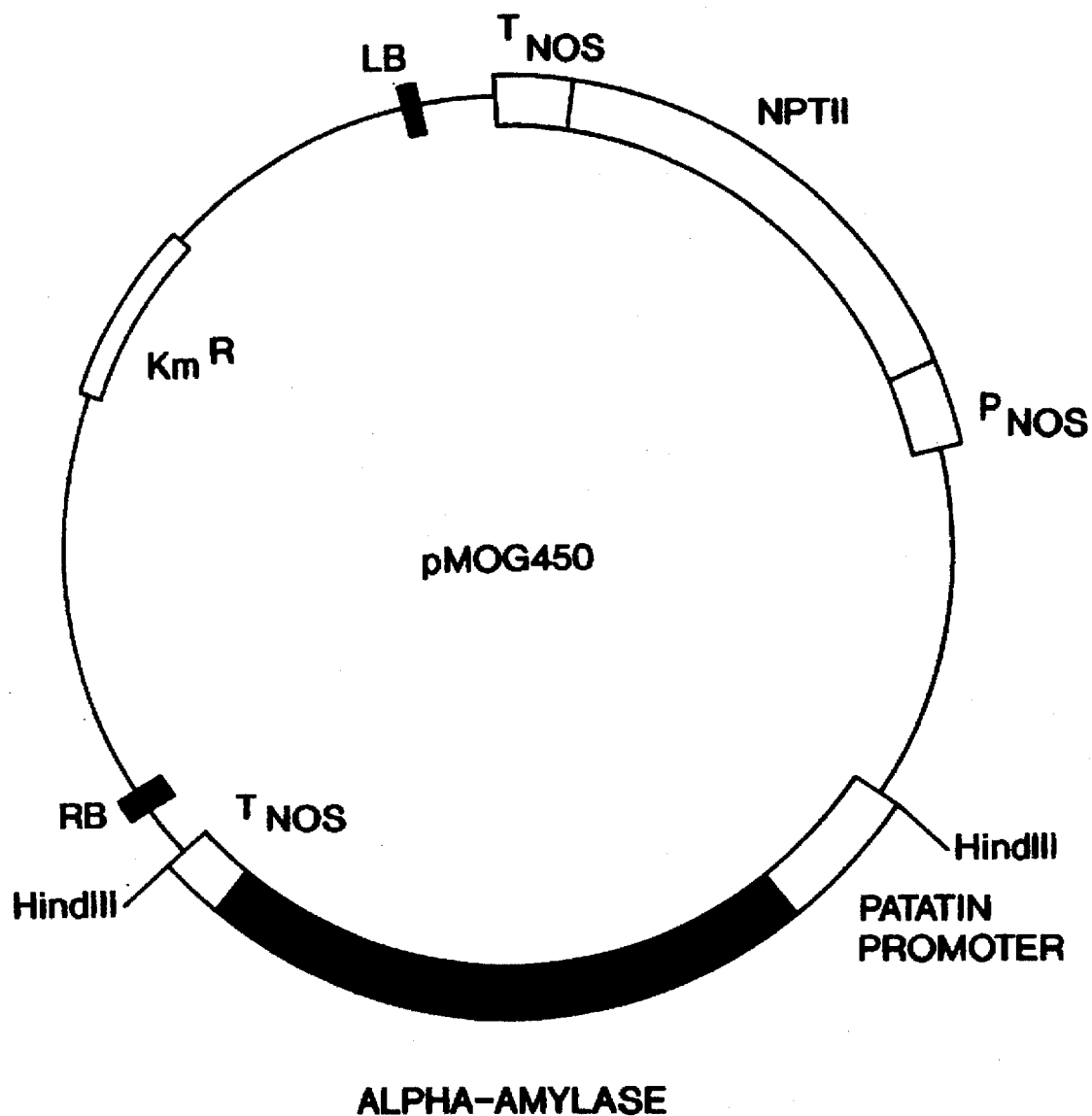
FIG. 5. Binary plasmid pMOG450, which comprises binary vector pMOG23 containing the genomic DNA sequence encoding mature α-amylase from *Bacillus licheniformis*, preceded by a methionine translation initiation codon and under the control of the class-I patatin promoter from potato.

The oligonucleotides are designed to contain suitable restriction sites (HindIII and NcoI) at their termini to allow assembly of the expression cassette after digestion of the fragments with the restriction enzymes. A fragment of about 1.3 kb containing a functional class-I patatin promoter fragment was synthesized. After addition of EcoRI synthetic linkers by ligation, the fragment was cloned in pUC18 linearized with EcoRI, resulting in plasmid pMOG546. In a three-way ligation, the HindIII/NcoI-fragment of plasmid pMOG546, together with the NcoI/HindIII fragment of plasmid pMOG322 (see Example 2, encoding mature α-amylase of *Bacillus licheniformis* preceded by an ATG translation initiation codon and followed by the nos terminator from *Agrobacterium tumefaciens*) were ligated into the binary vector pMOG23 cut with HindIII, resulting in the binary plasmid pMOG450 (see FIG. 5).

EXAMPLE 7

Transformation of Tomato

Tomato (*Lycopersicon esculentum* cv. Moneymaker) was transformed with the Agrobacterium strain LBA4404 (pMOG228). The basic culture medium consisted of MS-medium (Murashige & Skoog, 1962), supplemented with 30 g/L sucrose, B5 vitamins (Gamborg, 1970), 2 mg/L zeatin riboside and 0.1 mg/L indole acetic (IAA). The media were solidified where necessary with 0.7 g/L Daichin agar.

Cotyledons of six day old, axenically grown seedlings were cut on both ends and pre-incubated for 24 hours on solid medium with a feeder of a 10 day old Petunia cell suspension. The cotyledons were subsequently co-cultivated for 20 hours with a log-phase culture of *Agrobacterium tumefaciens* strain LBA4404 (pMOG228) which was washed with MS-medium. The cotyledons were dried briefly on sterile filter paper and placed on solid medium with a feeder layer of a 10 day old Petunia cell suspension. After 48 hours, the cotyledons were transferred to plates containing the same medium without the feeder layer and with 200 mg/L cefotaxim and 100 mg/L vancomycin. Five days after co-cultivation, the cotyledons were transferred to the same medium plus 100 mg/L kanamycin. The cotyledons were transferred to fresh plates every three weeks.

Shoots were excised and placed on rooting medium (MS-medium supplemented with 10 g/L sucrose, 100 mg/L cefotaxim and 50 mg/L vancomycin). After rooting, the plants were transferred to the soil and subsequently tested for α-amylase expression.

EXAMPLE 8

Expression of α-amylase From *Bacillus licheniformis* in Tomato and Carbohydrate Analysis of the Transgenic Fruit Transgenic tomato plants obtained from the transformation with the constitutive expression construct pMOG228 did not show phenotypic effects. Leaves of the transgenic tomato plants grown for three weeks in soil were assayed for α-amylase activity as described in Example 4. Expression levels of α-amylase in the plants analyzed varied between 0 and 1.2 U/μg soluble protein. The presence of the enzyme was confirmed with Western blotting using antibodies raised against *Bacillus licheniformis* α-amylase.

The starch content in leaves obtained from plants grown for 3 weeks in soil and collected half-way through the photoperiod was determined as described in Example 5. Transgenic plants expressing α-amylase contained demonstrably less starch in their leaves than control plants.

EXAMPLE 9

Cloning of a cDNA Encoding Mature Glucoamylase From *Aspergillus niger*

All transformations in *E.coli* in this example were performed in strain DH5α.

a. Isolation of poly A$^+$ RNA from *Aspergillus niger*

About 1×10$^8$ spores of *Aspergillus niger* strain DS 2975 (deposited at the Centraal Bureau voor Schimmelcultures on Aug. 10, 1988, under number CBS 513.88) are inoculated in 100 ml pre-culture medium containing (per liter): 1 g KH$_2$PO$_4$; 30 g maltose; 5 g yeast-extract; 10 g casein-hydrolysate; 0.5 g MgSO$_4$.7H$_2$O and 3 g Tween 80. The pH is adjusted to 5.5.

After growing overnight at 34° C. in a rotary shaker, 1 ml of the growing culture is inoculated in a 100 ml main-culture containing (per liter): 2 g KH$_2$PO$_4$; 70 g malto-dextrin (Maldex MDO$_3$, Amylure); 12.5 g yeast-extract; 25 g casein-hydrolysate; 2 g K$_2$SO$_4$; 0.5 g MgSO$_4$.7H$_2$O; 0.03 g ZnCl$_2$; 0.02 g CaCl$_2$; 0.05 g MnSO$_4$.4H$_2$O and FeSO$_4$. The pH is adjusted to 5.6. The mycelium is grown for 140 hours and harvested. 0.5 g of dry mycelium is frozen with liquid nitrogen and ground. The material is subsequently homogenized with an Ultra turrax (full speed, 1 minute) at 0° C. in 10 ml 3M LiCl, 6M Urea and maintained overnight at 4° C. as described by Auffray and Rougeon (1980). Total cellular RNA is obtained after centrifugation at 16,000 g and dissolved in 3 ml 10 mM Tris-HCl (pH 7.4), 0.5% SDS and extracting twice with phenol:chloroform:isoamylalcohol (50:48:2). The RNA is precipitated with ethanol and redissolved in 1 ml 10 mM Tris-HCl (pH 7.4), 0.5% SDS. For poly A$^+$ selection, the total RNA sample is heated for 5 minutes at 65° C., adjusted to 0.5M NaCl and subsequently applied to an oligo(dT)-cellulose column. After several washes with an solution containing 10 mM Tris pH 7.0, 0.5% SDS and 0.1 mM NaCl, the poly A$^+$ RNA is collected by elution with 10 mM Tris pH 7.0 and 0.5% SDS.

b. Preparation and cloning of a cDNA encoding glucoamylase

To synthesize the first strand of the cDNA, 5 µg of poly A$^+$ RNA, isolated according to Example 11a, is dissolved in 16.5 µl H$_2$O and the following components are added: 2.5 µl RNasin (30 U/µl ), 10 µl of a buffer containing 50 mM Tris, 6 mM MgCl$_2$ and 40 mM KCl, 2 µl 1M KCl, 5 µl 0.1M DTT, 0.5 µl oligo(dT)$_{12-18}$ (2.5 mg/ml), 5 µl 8 mM dNTP-mix, 5 µl BSA (1 mg/ml) and 2.5 µl Moloney MLV reverse transcriptase (200 U/µl). The mixture is incubated for 30 minutes at 37° C. and the reaction is stopped by adding 10 µl 0.2M EDTA and 50 µl H$_2$O. An extraction is performed using 110 µl chloroform and following centrifugation for 5 minutes, the aqueus layer is collected and 110 µl 15M NH$_4$Ac and 440 µl absolute ethanol (temperature: −20° C.) are added. Precipitation is performed in a dry ice/ethanol solution for 30 minutes. Following centrifugation for 10 minutes at 0° C., the cDNA/mRNA pellet is washed with 70% ice-cold ethanol. The pellet is dried and dissolved in 20 µl of H$_2$O.

Isolation of a cDNA encoding glucoamylase is performed with the Polymerase Chain Reaction. Two oligonucleotides are synthesized, based on the nucleotide sequence of glucoamylase G1 cDNA published by Boel et al. (1984).

Oligo 1: 5' CTTCCACCATGGCGACCTTGGATTC 3' (SEQ ID NO:8)

Oligo 2: 5' AGCTCGAGCTCACCGCCAGGTGTC 3' (SEQ ID NO:9)

With these two oligonucleotides, the region encoding the mature enzyme, i.e. without secretory signal peptide and pro-peptide, preceded by a translation initiation ATG codon (underlined) and flanked by suitable cloning sites is amplified. The obtained DNA is digested with NcoI and SstI. Together with the SstI/HindIII-fragment of p35SGUSINT (Vancanneyt et al., 1990) containing the terminator transcript fragment of the CaMV 35S, the NcoI/SstI fragment is cloned in a three-way ligation into pMOG18 (see Example 2), which is digested with NcoI and HindIII, resulting in plasmid pMOG567.

The PstI/SstI-fragment of pMOG567 is subsequently cloned in pIC2OH (Marsh et al., 1984), digested with PstI and SstI. In the resulting plasmid, the PstI/HindIII-fragment is replaced by the corresponding amyloglucosidase cDNA-fragment, resulting in pMOG568. The sequence of the HindIII/SstI fragment is compared to the sequence published by Boel et al. (1984). The PstI/SstI-fragment of pMOG568 is ligated to the PstI/StyI-fragment of the amyloglucosidase cDNA, and the resulting fragment is cloned in a three-way ligation, together with a synthetic adaptor:

5' CATGGCGAC 3' (SEQ ID NO:10)

3' CGCTGGAAC 5' (SEQ ID NO:11)

into pMOG567 digested with NcoI and SstI, resulting in plasmid pMOG569 which encodes mature amyloglucosidase under control of the CaMV 35S promoter and terminator.

EXAMPLE 10

Cloning of Both α-amylase From *Bacillus licheniformis* and Glucoamylase From *Aspergillus niger*

All transformations in this example are performed in *E. coli* strain DH5α.

The HindIII/NcoI class-I patatin promoter fragment (see Example 6) from plasmid pMOG546 is cloned, together with the NcoI/HindIII fragment of plasmid pMOG567 encoding mature amyloglucosidase from *Aspergillus niger* and the CaMV 35S terminator fragment (see Example 11), into pIC19R (Marsh et al., 1984) linearized with HindIII, resulting in plasmid pMOG440.

Plasmid pMOG450 (see Example 6) is digested with HindIII. The HindIII fragment, containing the class-I patatin promoter, the DNA fragment encoding mature α-amylase from *Bacillus licheniformis* and the nos terminator from *Agrobacterium tumefaciens*, is cloned in the binary vector pMOG23 linearized with HindIII. This results in the binary vector pMOG436.

Figure 6:
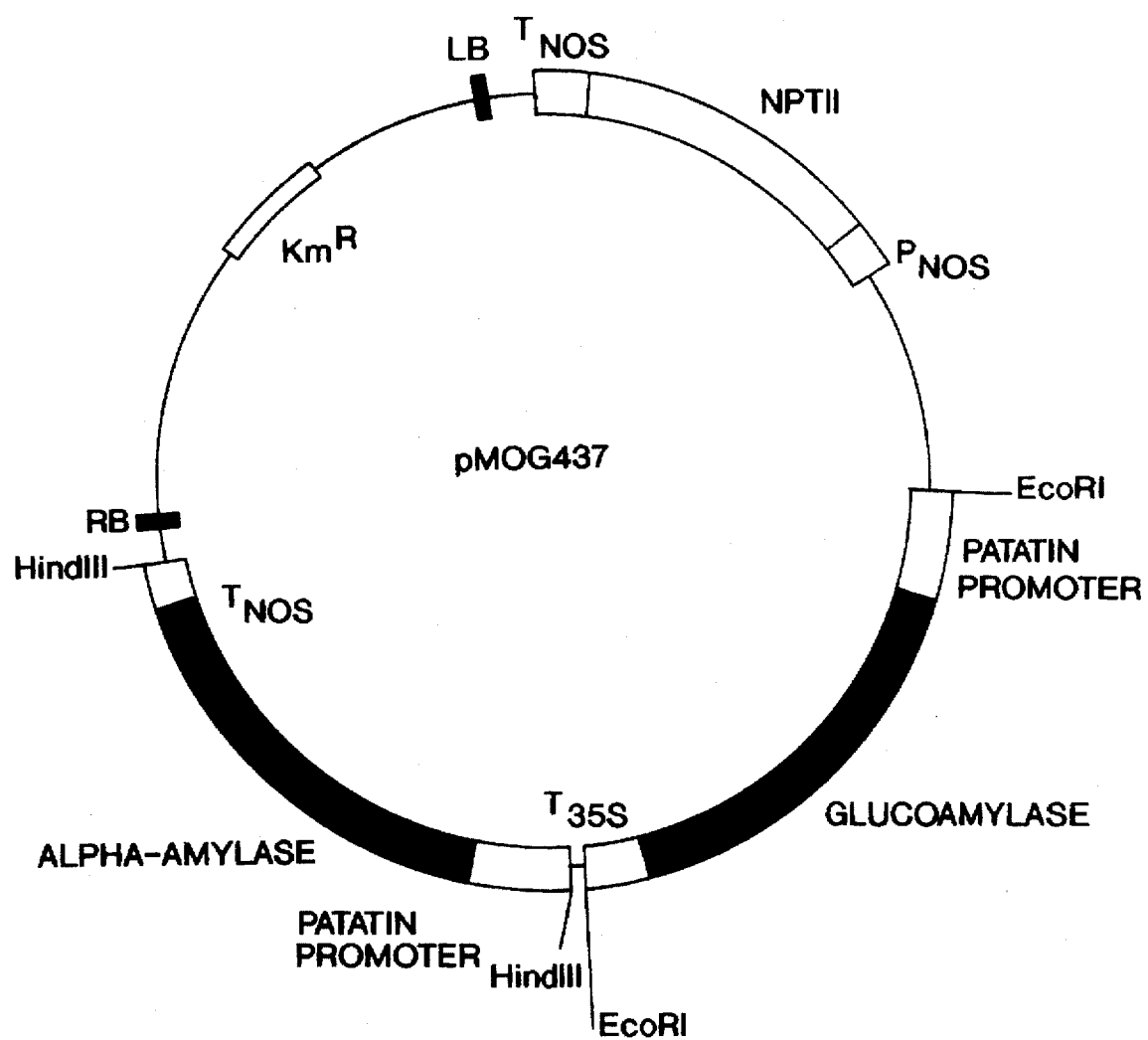
FIG. 6. Binary plasmid pMOG437, which comprises binary vector pMOG23 containing DNA sequences encoding mature α-amylase from *Bacillus licheniformis* and mature glucoamylase from *Aspergillus niger*, both preceeded by a methionine translation initiation codon and both under the control of a class-I patatin promoter from potato.

Plasmid pMOG440 is digested with EcoRI. The EcoRI fragment, containing the class-I patatin promoter, the cDNA fragment encoding mature glucoamylase from *Aspergillus niger* and the CaMV 35S terminator, is cloned in the binary plasmid pMOG436, linearized with EcoRI. Using restriction enzyme analysis, transformants are screened for the presence of the two expression cassettes in a tandem orientation. The binary vector with the expression cassettes having this orientation, called pMOG437 (FIG. 6) is used for transformation experiments.

The chimeric α-amylase gene from *Bacillus licheniformis* and the chimeric glucoamylase gene from *Aspergillus niger*, both under the control of the tuber-specific class-I patatin promoter, as present on the binary plasmid pMOG437, are mobilized in a triparental mating with the *E. coli* strain HB101 containing plasmid pRK2013 (Ditta et al., 1980) into Agrobacterium strain LBA4404 which contains a plasmid having the virulence genes necessary for T-DNA tranfer to the plant (Hoekema et al., 1983).

EXAMPLE 11

Transformation of Potato

Potato (*Solanum tuberosum* cv. Désiree) was transformed with the Agrobacterium strain LBA4404 (pMOG437) as described by Hoekema et al. (1989).

The basic culture medium was a MS30R3-medium, consisting of MS-medium (Murashige & Skoog, 1962), supplemented with 30 g/L sucrose and with R3-vitamins (0 oms et al., 1987) and, where indicated, 5 µM zeatin riboside (ZR) and 0.3 µM indole acetic acid (IAA). The media were solidified where necessary with 0.7 g/L Daichin agar.

Tubers of *Solanum tuberosum* cv. Désiree were peeled and surface-sterilized for 20 minutes in 0.6% hypochlorite solution containing 0.1% Tween-20. The potatoes were washed thoroughly in large volumes of sterile water for at least 2 hours. Discs of approximately 2 mm thickness were sliced from cylinders of tuber tissue prepared with a corkbore. Discs were incubated for 20 minutes in a suspension consisting of the MS30R3-medium without ZR and IAA, containing between $10^6$–$10^7$ bacteria/ml of Agrobacterium LBA4404 (pMOG437). The discs were subsequently blotted dry on sterile filter paper and transferred to solid MS30R3-medium with ZR and IAA. Discs were transferred to fresh medium with 100 mg/L cefotaxim and 50 mg/L vancomycin after 2 days. A week later, the discs were again transferred to the same medium but this time 100 mg/L kanamycin was present to select for transgenic shoots. After 4–8 weeks, shoots emerged from the discs at a frequency of 5–10 shoots per 100 discs. Shoots were excised and placed on rooting medium (MS30R3-medium without ZR and IAA, but with 100 mg/L cefotaxim and 100 mg/L kanamycin), and propagated axenically by meristem cuttings and transferred to soil. The plants were allowed to tuberize and were subsequently tested for expression of the genes of interest.

EXAMPLE 12

Simultaneous Tuber-specific Expression of Both α-amylase (*Bacillus licheniformis*) and Glucoamylase (*Aspergillus niger*) in Potato and Carbohydrate Analysis of Transgenic Tubers Potato plants are transformed with binary vector pMOG437 as described in Example 7. The plants are assayed for both α-amylase and glucoamylase activity. Alpha-amylase activity is determined as described in Example 4. The presence of glucoamylase is demonstrated by Western blotting, using antibodies raised against *Aspergillus niger* glucoamylase. Plant material (about 50 mg) is homogenized in 100 µl assay buffer and homogenized. The homogenate is spun for 10 minutes in an Eppendorf centriguge. The supernatant is tested for α-amylase activity, for the presence of glucoamylase and for protein content. The presence of the enzymes is only detected in the tubers of the transgenic potatoes.

Tubers of transgenic potatoes expressing both enzymes are analyzed for the presence of soluble sugars by HPLC. A higher content of soluble sugars is found in transgenic tubers as compared to control plants.

INDEX OF CITED REFERENCES

Auffray, C. & Rougeon, F. (1980) Eur. J. Biochem. 107,303.

Baulcombe, D. C., Saunders, G. R., Bevan, M. W., Mayo, M. A. & Harrison, B. D. (1986) Nature 321, 446.

Bevan, M. (1984) Nucl. Acids Res. 12, 8711.

Bevan, M., Barker, R., Goldsbrough, A., Jarvis, M., Kavanagh, T. & Iturriaga (1986) Nucl. Acids Res. 14, 4625.

Bhattacharyya, M., Smith, A. M., Ellis, T. H. N., Hedley, C. & Martin, C. (1990) Cell 60, 115

Bird, C. R., Smith, C. J. S., Ray, J. A., Moureau, P., Bevan, M. W., Bird, A. S., Hughes, S., Morris, P. C., Grierson, D. & Schuch, W. (1988) Plant Mol. Biol. 11, 651.

Boel, E., Hjort, I., Svensson, B., Norris, F., Norris, K. E. & Fiil, N. P. (1984) EMBO J., 3, 1097–1102.

Brederode, F. T., Koper-Zwarthoff, E. C. & Bol, J. F. (1980) Nucl. Acids Res. 8, 2213.

Caspar, T., Huber, S. C. & Somerville, C. (1985) Plant Physiol. 79, 11.

Caspar, T., Lin, T. -P., Monroe, J., Bernhard, W., Spilatro, S., Preiss, J. & Somerville, C. (1989) Proc. Natl. Acad. Sci. USA 86, 5830.

Coruzzi, G., Broglie, R., Edwards, C., Chua, N. -H. (1984) EMBO J. 3, 1671–1679.

Ditta, G., Stanfield, S., Corbin, D. & Helinski, D. R. (1980) Proc. Natl. Acad. Sci. USA, 77, 7347.

Fraley, R. T., Rogers, S. G., Horsch, R. B. (1986) CRC Critical Reviews In Plant Sciences 4, 1–46.

Gamborg, O. L. (1970) Plant Physiol., 45, 372.

Gordon-Kamm, W. J., Spencer, T. M., Mangano, M. L., Adams, T. R., Daines, R. J., Start, W. G., O'Brien, J. V., Chambers, S. A., Adams Jr., W. R., Willets, N. G., Rice, T. B., Mackey, C. J., Krueger, R. W., Kausch, A. P. & Lemaux, P. G. (1990) The Plant Cell 2, 603.

Guilley, H., Dudley, R. K., Jonard, J., Balazs, E. & Richards, K. E. (1982) Cell 30, 763.

Hanson, H. R. & McHale, N. A. (1988) Plant Physiol. 88, 838.

Hoekema, A., Hirsch, P. R., Hooykaas, P. J. J. & Schilperoort, R. A. (1983) Nature 303, 179.

Hoekema, A., Huisman, M. J., Molendijk, L., Van den Elzen, P. J. M. & Cornelissen, B. J. C. (1989) Bio/Technology 7, 273.

Horsch, R. B., Fry, J. E., Hoffmann, N. L., Eichholtz, D., Rogers & S. G. & Fraley, R. T. (1985) Science 227, 1229.

Hovenkamp-Hermelink, J. H. M., Jacobsen, E., Ponstein, A. S., Visser, R. G. F., Vos-Scheperkeuter, G. H., Bijmolt, E. W., De Vries, J. N., Witholt, B. & Feenstra, W. J. (1987) Theor. Appl. Genet., 75, 217.

Jefferson, R. A. (1987) Plank Mol. Biol. Rep. 5, 387.

Kay, R., Chan, A., Dayly, M. & McPherson, J. (1987) Science 236, 1299.

Lacks, S. A. & Springhorn, S. S. (1980) J. Biol. Chem. 255, 7467.

Lee, B., Murdoch, K., Topping, J., Kreis, M. & Jones, M. G. K. (1989) Plant Mol. Biol. 13, 21.

Lin, T-P., Spilatro, S. R. & Preiss, J. (1988a) Plant Physiol. 86, 251.

Lin, T-P., Caspar, T., Somerville, C. & Preiss, J. (1988b) Plant Physiol. 86, 1131.

Lin, T-P., Caspar, T., Somerville, C. & Preiss, J. (1988c) Plant Physiol. 88., 1175.

Marsh, J. L., Erfle, M. & Wykes, E. J. (1984) Gene 32, 481.

Mettler, I. J. (1987) Plant Mol. Bil. Rep. 5, 346.

Mignery, G. A., Pikaard, C. S. & Park, W. D. (1988) Gene, 62, 27.

Murashige, T. & Skoog, F. (1962) Physiol. Plant. 14, 473.

Okita, T. W., Greenberg, E., Kuhn, D. N. & Preiss, J. (1979) Plant Physiol. 64, 187.

Ooms, G., Burrell, M. M., Karp, A., Bevan, M. & Hille, J. (1987) Theor. Appl. Genet. 73, 744.

Potrykus, I. (1990) Bio/Technol. 8, 535.

Rocha-Sosa, M., Sonnewald, U., Frommer, W. B., Stratman, M., Schell, J., & Willmitzer, L. (1989) EMBO J. 8, 23.

Ryan, A. J., Royal, C. L., Hutchinson, J. & Shaw, C. H. (1989) Nucl. Acids Res. 17, 3584.

Saito, N. (1973) Arch. Biochem. Biophys. 155, 290.

Schreier, P. H., Seftor, E. A., Schell, J, and Bohnert, H. J. (1985) EMBO J. 4, 25–32.

Schilperoort, R. A., Hoekema, A. & Hooykaas, P. J. J. (1984) European Patent Application No. EP-A 0 120 516.

Shimamoto, K., Terada, R., Izawa, T. & Fujimoto, H. (1989) Nature 338, 274.

Sijmons, P. C., Dekker, B. M. M., Schrammeijer, B., Verwoerd, T. C., Van Den Elzen, P. J. M. & Hoekema, A. (1990) Bio/Technology 8, 217.

Shannon, J. C. & Garwood, D. L. (1984) In: Starch. Chemistry and technology. p. 25. (Whistler, R. L. et al., eds.). Academic Press Inc., Orlando.

Smeekens, S., Weisbeek, P., Robinson, C. (1990) T. I. B. S. 15, p.73.

Tague, B. W. & Chrispeels, M. J. (1988) Plant Phys. 86, 506.

Tingey, S. V., Walker, E. L. & Coruzzi, G. M. (1987) EMBO J. 6, 3565–3669.

Vancanneyt, G., Schmidt, R., O'Connor-Sanchez, A., Willmitzer, L. & Rocha-Sosa, M. (1990) Mol. Gen. Genet., 220, 245.

Van den Broeck, G., Timko, M. P., Kausch, A. P., Cashmore, A. R., Van Montagu, M., Herrera-Estrella, L. (1985) Nature 313, 358–363.

Vasil, V., Redway, F. & Vasil, I. K. (1990) Bio/Technol. 8, 429.

Vasil, V, Brown, S. M., Re, D., Fromm, M. E., and Vasil, I. K. (1991) Bio/Technol., 9, 743.

Wenzler, H. -C., Miguery, G. A., Fisher, L. H. & Park, W. D. (1989) Plant Mol. Biol. 12, 41.

---

We claim:

1. A method for modifying the carbohydrate composition of a plant or plant organ, wherein said method comprises growing a stably transformed, transgenic plant containing a recombinant DNA expression construct encoding a microbial alpha-amylase under conditions wherein said alpha-amylase-encoding construct is expressed and the carbohydrate composition of said plant or plant organ is modified.

2. The method of claim 1, wherein said expression construct comprises a regulatory sequence operably linked to a nucleotide sequence encoding said alpha-amylase, which regulatory sequence directs expression of said alpha-amylase-encoding nucleotide sequence at a selected stage of development or maturity of the transgenic plant or plant organ.

3. The method of claim 1 wherein said expression construct contains a regulatory sequence operably linked to a nucleotide sequence encoding said alpha-amylase, which regulatory sequence directs tissue-specific expression of said alpha-amylase-encoding nucleotide sequence in the transgenic plant or plant organ.

4. The method of claim 1 wherein the DNA expression construct comprises a nucleotide sequence encoding a fusion protein consisting of a leader amino acid sequence which is fused to said alpha-amylase, and wherein the leader amino acid sequence targets the alpha-amylase to a cellular compartment or organelle.

5. The method of claim 1 wherein said transgenic plant contains at least one expression cassette which contains a nucleotide sequence encoding a second microbial enzyme.

6. The method of claim 5 wherein said second microbial enzyme is glucoamylase.

7. The method of claim 1 wherein said α-amylase originates from *Bacillus licheniformis*.

8. A recombinant DNA expression cassette comprising a regulatory sequence operably linked to a nucleotide sequence encoding a microbial enzyme selected from the group consisting of alpha-amylase and glucoamylase, which regulatory sequence directs expression of said enzyme-encoding nucleotide sequence at a selected stage of development or maturity of a transgenic plant or plant organ.

9. A recombinant DNA expression cassette comprising a 35S CaMV promoter operably linked to a nucleotide sequence encoding a microbial enzyme selected from the group consisting of alpha-amylase and glucoamylase.

10. A recombinant DNA expression cassette comprising a regulatory sequence operably linked to a nucleotide sequence encoding a microbial enzyme selected from the group consisting of alpha-amylase and glucoamylase, which regulatory sequence directs tissue-specific expression of said enzyme-encoding nucleotide sequence in a plant.

11. A vector comprising an expression cassette according to any of the claims 8–10.

12. A stably transformed, transgenic plant characterized in that said plant contains an expression cassette encoding a microbial alpha-amylase according to any one of claims 8–10.

13. A bacterial strain characterized in that said bacterial strain contains a vector according to claim 11.

14. A stably transformed, transgenic plant or plant organ, characterized in that said plant or plant organ contains a modified carbohydrate composition, said plant or plant organ being made by the method of either claim 1 or claim 5.

15. The method of claim 5 wherein said second microbial enzyme uses the degradation products resulting from the action of said first enzyme as a substrate.

16. The method of claim 10 wherein the glucoamylase originates from *Aspergillus niger*.

17. The method of any one of claims 1–4, 5–7 and 15–16, wherein said transgenic plant is selected from the group consisting of tomato, potato, corn, cassava carrot, lettuce, strawberry and tobacco.

* * * * *

UNITED STATES PATENT AND TRADEMARK OFFICE

CERTIFICATE OF CORRECTION

PATENT NO. : 5,705,375

DATED : 6 January 1998

INVENTOR(S) : Albert J. J. VAN OOYEN et al.

It is certified that error appears in the above-identified patent and that said Letters Patent is hereby corrected as shown below:

Title page,
Please add the second assignee in this case:

Item --[73] Assignee: GIST-BROCADES, N.V., Netherlands--

Signed and Sealed this

Thirty-first Day of October, 2000

*Attest:*

Q. TODD DICKINSON

*Attesting Officer*   *Director of Patents and Trademarks*